US007892783B2

(12) United States Patent
Monget et al.

(10) Patent No.: US 7,892,783 B2
(45) Date of Patent: Feb. 22, 2011

(54) CULTURE MEDIUM FOR DETECTING AND IDENTIFYING *VIBRIO* BACTERIA

(75) Inventors: Daniel Monget, Saint-Sorlin-En-Bugey (FR); Denis Robichon, Blyes (FR)

(73) Assignee: Biomerieux, Marcy l'Etoile (FR)

( * ) Notice: Subject to any disclaimer, the term of this patent is extended or adjusted under 35 U.S.C. 154(b) by 91 days.

(21) Appl. No.: 11/918,663

(22) PCT Filed: May 16, 2006

(86) PCT No.: PCT/FR2006/050446
§ 371 (c)(1),
(2), (4) Date: Oct. 17, 2007

(87) PCT Pub. No.: WO2007/000530
PCT Pub. Date: Jan. 4, 2007

(65) Prior Publication Data
US 2009/0047698 A1 Feb. 19, 2009

(30) Foreign Application Priority Data
May 18, 2005 (FR) .................... 05 51283

(51) Int. Cl.
*C12Q 1/04* (2006.01)
(52) U.S. Cl. ........................ 435/34; 435/909
(58) Field of Classification Search .......... 435/34, 435/909
See application file for complete search history.

(56) References Cited
U.S. PATENT DOCUMENTS

| 4,308,346 | A * | 12/1981 | Niwano ........................ 435/34 |
| 6,265,203 | B1 * | 7/2001 | Ushiyama ................ 435/253.6 |
| 2002/0110848 | A1 * | 8/2002 | Bochner et al. .............. 435/34 |
| 2002/0192742 | A1 * | 12/2002 | Ushiyama et al. ............ 435/34 |
| 2004/0265946 | A1 * | 12/2004 | Rambach ..................... 435/34 |
| 2005/0196825 | A1 * | 9/2005 | Roth et al. .................... 435/34 |

FOREIGN PATENT DOCUMENTS
WO  WO 02/00922 A1  1/2002

OTHER PUBLICATIONS

Miyamoto T. et al. Improved Fluorogenic Assay for Rapid Detection of *V. parahaemolyticus* in Foods. Appled and Environmental Microbiology 56(5)1480-4, May 1990.*
Miyamoto, Takahisa et al., "Improved Fluorogenic Assay for Rapid Detection of *Vibrio parahaemolyticus* in Foods," Applied and Environmental Microbiology, vol. 56, No. 5, XP-002365823, p. 1480-1484 (May 1990).
Chatterjee, B.D. et al., "Studies on the Beta-D-galactosidase Activity of *Vibrio parahaemolyticus*," Indian J. Med. Res. vol. 60, XP-001003086, p. 831-833 (Jun. 6, 1972).
Kaper, James B. et al., "Cholera," Clinical Microbiology Reviews, vol. 8, No. 1, XP-002365824, p. 48-86 (Jan. 1995).
Amaro, Carmen et al., "*Vibrio vulnificus* Biotype 2, Pathogenic for Eels, Is Also an Opportunistic Pathogen for Humans," Applied and Environmental Microbiology, vol. 62, No. 4, p. 1454-1457 (Apr. 1996).
Donovan, Terence J. et al., "Culture Media for the Isolation and Enumeration of Pathogenic *Vibrio* Species in Foods and Environment Samples," Int. J. Food Microbiology, vol. 26, p. 77-91 (1995).

* cited by examiner

*Primary Examiner*—Ralph Gitomer
(74) *Attorney, Agent, or Firm*—Oliff & Berridge, PLC

(57) ABSTRACT

The present invention relates to a reaction medium for *cholerae*-group *Vibrio* (*cholerae/vulnificus* and *mimicus*) and *Vibrio parahaemolyticus* bacteria, comprising
  a substrate for detecting a β-galactosidase enzymatic activity,
  a sugar,
  a coloured indicator.

The invention also relates to the use of this medium for isolating and identifying *cholerae*-group *Vibrio* (*cholerae/vulnificus* and *mimicus*) and *Vibrio parahaemolyticus*.

Finally, the invention relates to a method for identifying *Vibrio cholerae* and *Vibrio parahaemolyticus* bacteria, according to which beta-galactosidase activity is detected for identifying *Vibrio cholerae* and the acidification of a sugar is detected for revealing *Vibrio parahaemolyticus*.

10 Claims, No Drawings

US 7,892,783 B2

CULTURE MEDIUM FOR DETECTING AND IDENTIFYING *VIBRIO* BACTERIA

The present invention relates to culture medium for detecting *Vibrio* bacteria. The invention also relates to the use of this medium, and also to a method for identifying *Vibrio* bacteria.

Cholera is a highly contagious diarrheic disease due to a Gram-negative bacillus, *Vibrio cholerae*. Similarly, *Vibrio parahaemolyticus* is responsible for acute gastroenteritis. The bacterial strains responsible for these pathologies are transmitted orally in contaminated water or foods. Due to the epidemic nature of these diseases, it is frequently necessary to detect these bacteria in contaminated patients, or in environments such as foods and water.

The reference medium currently used for detecting *Vibrio* is the TCBS (Thiosulfate Citrate Bile salt Saccharose) medium. TCBS agar is a selective medium, recommended for searching for and isolating pathogenic *Vibrio* (standard NF ISO 8914 and World Health Organization recommendations). The high concentration of bile and of citrate, associated with a high pH (pH=8.6) makes it possible to eliminate many bacteria. The main carbon source is saccharose. The use of the saccharose is reflected by a decrease in pH, and by the pH indicator changing colour from green to yellow. Saccharose-positive colonies, such as several species of *Vibrio*, in particular *V. cholerae*, therefore appear yellow. Saccharose-negative colonies, such as *V. parahaemolyticus*, appear green. However, this medium is not very sensitive, nor is it very specific, and many false positives are detected (i.e. bacteria are detected which are considered to be *Vibrios*, although they are not).

The CHROMagar *Vibrio* medium also exists. This selective chromogenic medium makes it possible to differentiate *V. parahaemolyticus*, *V. vulnificus* and *V. cholerae* with respect to the other species of *Vibrio*. *V. parahaemolyticus* appears in the form of purple colonies, *V. vulnificus* and *V. cholerae* produce blue colonies, whereas other species such as *V. alginolyticus* form colourless colonies. This medium is in the form of a powder. The principle of this medium is based on the simultaneous detection of β-glucosidase activity, specific for *V. parahaemolyticus*, and β-galactosidase activity, specific for *V. cholerae* and *V. vulnificus*, in the presence of a high concentration of sucrose. However, in addition to some species identified as being false positives, this medium has a moderate sensitivity for detection of *V. cholerae*.

The invention proposes to solve the shortcomings of the prior art by providing a sensitive and specific culture medium for isolating and identifying *cholerae*-group *Vibrio* (*cholerae*/*vulnificus* and *mimicus*) and *Vibrio parahaemolyticus*.

In this respect, the invention relates to a reaction medium for *cholerae*-group bacteria (*cholerae/vulnificus* and *mimicus*) and *Vibrio parahaemolyticus* bacteria, comprising a substrate for detecting a β-galactosidase enzymatic activity, a sugar, a coloured indicator.

For the purpose of the present invention, the term "reaction medium" is intended to mean a medium comprising all the elements required for the survival and/or growth of microorganisms.

This reaction medium can either serve only as a visualizing medium, or as a culture and visualizing medium. In the first case, the culturing of the microorganisms is carried out before inoculation and, in the second case, the reaction medium also constitutes the culture medium. The reaction medium may be solid, semi-solid or liquid. The term "solid medium" is intended to mean, for example, a gelled medium. Preferably, this medium consists of a gelled medium. Agar is the conventional gelling agent in microbiology for culturing microorganisms, but it is possible to use gelatin or agarose. A certain number of preparations are commercially available, for instance Columbia agar, Trypcase-soy agar, MacConkey agar, Sabouraud agar or more generally those described in the Handbook of Microbiological Media (CRC Press).

The culture medium according to the invention may contain other optional additives such as, for example: peptones, one or more growth factors, carbohydrates, one or more selective agents, buffer solutions, one or more gelling agents, etc. This culture medium can be in the form of a liquid, or of a ready-to-use gel, i.e. ready for inoculation in a tube or flask, or in a Petri dish. When the presentation form is in a flask, a prior regeneration (passage at 100° C.) of the medium is preferably carried out, before pouring into a Petri dish. The medium according to the invention is preferably a selective medium, i.e. a medium comprising inhibitors of growth of the bacteria and yeasts that it is desired to detect.

For the purpose of the present invention, the substrate is chosen from any substrate that can be hydrolyzed to a product which allows the direct or indirect detection of a β-galactosidase enzymatic activity. Preferably, this substrate comprises a first part specific for the enzymatic activity to be revealed. This first part is capable of interacting with said enzyme, which is specific for the microorganism being sought, a second part which acts as a label, hereinafter referred to as label part, which may be fluorescent or chromogenic.

As fluorescent substrate, mention may in particular be made of substrates based on umbelliferone or on aminocoumarin, based on resorufin or else based on fluorescein.

The enzymatic substrates of the invention can be used in a broad pH range, in particular between pH 5.5 and 10.

The concentration of enzymatic substrate of the invention in the reaction medium is between 0.01 and 2 g/l, and it is advantageously 0.075 g/l. In fact, at this substrate concentration, a better coloration contrast is obtained.

According to a preferred embodiment of the invention, said substrate is an X-β-galactosidase chromogenic substrate, with X representing the label part. Preferably, the substrate used is 5-bromo-4-chloro-3-indoxyl-beta-D-galactopyranoside. Preferably, this substrate is present in the medium at a concentration of between 0.01 and 2 g/l, preferably between 0.05 and 1.15 g/l.

According to another embodiment of the invention, the substrate can be chosen from β-galactosidase substrates such as RedA-β-galactosidase, Magenta-β-galactosidase, GreenA-β-galactosidase, Rose-β-galactosidase and Alizarine-β-galactosidase, which are sensitive for the detection of *V. cholerae*.

According to a preferred embodiment of the invention, the sugar is L-arabinose. Preferably, this sugar is present in the medium at a concentration of between 1 and 30 g/l, preferably between 5 and 15 g/l. Preferably, the concentration is approximately 8 g/l. The sugar can also be chosen from the following sugars: D-mannose, D-ribose, D-cellobiose, D-glucose, glucuronate and galactose.

According to a preferred embodiment of the invention, the coloured indicator is neutral red. Preferably, this coloured indicator is present in the medium at a concentration between 0.0001 and 0.05 g/l, preferably between 0.002 and 0.010 g/l, preferably between 0.003 and 0.007 g/l. The coloured indicator can also be bromothymol blue. According to a preferred embodiment of the invention, the concentration is approximately 0.010 g/l.

According to a specific embodiment of the invention, the reaction medium also comprises a second sugar, in order to improve the specificity of detection of *Vibrio parahaemolyticus* and *Vibrio cholerae* relative to the other bacterial species that may be present in the medium. Preferably, this second sugar is glucuronate. Preferably, this sugar is present in the medium at a concentration between 1 and 30 g/l, preferably between 5 and 15 g/l. Preferably, the concentration is approximately 8 g/l.

The invention also relates to the in vitro use of the medium as defined above, for isolating and identifying *cholerae*-group *Vibrio* (*cholerae/vulnificus* and *mimicus*) and *Vibrio parahaemolyticus*.

When this medium is used, the *Vibrio cholerae* are detected by means of a specific β-galactosidase activity which makes it possible to obtain blue-to-green colonies. The *Vibrio parahaemolyticus* are revealed through the specific use of L-arabinose which makes it possible to obtain pink colonies (very intense coloration) resulting from an acidification in the medium which causes the coloured indicator (neutral red) to change from colourless to bright pink. In the presence of bile salts, the coloration remains concentrated at the colony, which facilitates the reading of the media. The other *Vibrio* species appear violet or colourless.

Finally, the invention relates to a method for identifying *Vibrio cholerae* and *Vibrio parahaemolyticus* bacteria, in vitro, according to which beta-galactosidase activity is detected for identifying *Vibrio cholerae* and the acidification of a sugar is detected for revealing *Vibrio parahaemolyticus*.

According to a preferred embodiment of the invention, the beta-galactosidase activity for identifying *Vibrio cholerae* is detected using a chromogenic substrate specific for beta-galactosidase activity. This substrate is as defined above, and is preferably X-β-galactoside. According to a preferred embodiment of the invention, acidification of a sugar is detected using a coloured indicator, preferably neutral red, which changes colour during the variation in pH induced by the acidification of the sugar.

The following examples are given by way of illustration and are in no way limiting in nature. They will make it possible to understand the invention more clearly.

1. Choice of Strains and of Food Samples a—Evaluation of the Medium Using Pure Strains:

The medium according to the invention was tested on 69 strains, including 22 strains of *Vibrio* (8 *V. cholerae*, 2 *V. mimicus*, 2 *V. vulnificus*, 4 *V. parahaemolyticus*, 2 *V. alginolyticus*, 2 *V. fluvialis*, 1 *V. hollisae* and 1 *V. metschnikovii*); 8 strains of *Staphylococcus*; 6 strains of *Pseudomonas*; 6 strains of *Candida*; 4 strains of *Enterococcus*; 3 strains of *Enterobacter*; 2 strains of *Escherichia coli*; 2 strains of *Klebsiella*; 2 strains of *Proteus*; 2 strains of *Salmonella*; 2 strains of *Shigella*; 2 strains of *Yersinia*; 2 strains of *Aeromonas*; 2 strains of *Moraxella*; 2 strains of *Plesiomonas*; 1 strains of *Listeria*; 1 strain of *Acinetobacter*.

b—Evaluation of the Medium Using Artificially Contaminated Foods:

The following 4 food matrices: oysters, prawns, deep-frozen sea bass fillet and whole sea trout, were contaminated with *V. cholerae*. The other 5 matrices, ling fillet, frozen Mediterranean prawns, mussels, fish paté and surimi, were contaminated with *V. parahaemolyticus*.

The protocol used is that described by the standards NF ISO 8914 and NF EN ISO 6887-3, which recommend a pre-enrichment for 7 to 8 h at 37° C. in saline peptone water (SPW). The artificial contaminations are carried out using a bacterial suspension at 0.5 McFarland diluted to $10^{-5}$. A volume of 1 ml or 0.1 ml of this dilution is used to contaminate respectively the fish/other crustaceans and the shellfish; this contamination taking place after grinding of the food matrices in SPW and storage for 24 h at 2-8° C., but before the incubation for 7-8 h at 37° C. A sample of 10 µl of each pre-enrichment is then plate out on the medium according to the invention, which is incubated at 37° C. for 48 h. In parallel, a control test is carried out under the same conditions as above, but without artificial contamination. This makes it possible to verify, firstly, the natural flora of each matrix and, secondly, to be sure that no incompatibility exists between the medium according to the invention and the detection of the *Vibrio* colonies.

2. Preparation According to the Invention

The medium according to the invention is a selective medium comprising, as base medium, the trypcase-soy medium (bioMérieux ref. 43 011), and comprising the following elements (g/l)

| | |
|---|---|
| IPTG (IsoPropyl ThioGalactopyranoside) | 0.05 |
| Bile salts | 0.6 |
| Neutral red | 0.005 |
| L-arabinose | 10 |
| 5-Bromo-4-chloro-3-indoxyl-beta-D-galactopyranoside | 0.1 |

A second sugar (glucuronate; 10 g/l) is also added in order to improve the specificity of detection of *Vibrio parahaemolyticus* and *Vibrio cholerae*.

3. Inoculation of the Media Using Pure Strains

The strains of bacteria and yeasts, all derived from the applicant's collection, suspended in physiological saline, were inoculated so as to give isolated colonies on the medium. The dishes were incubated at 37° C. for 48 hours. The colonies formed were examined visually after 24 and more than 40 hours of incubation. The intensity of coloration of these colonies was evaluated and each strain was then classified positive or negative (expressing or not expressing the phenotype being sought), in the knowledge that a strain is considered to be positive for coloration intensity values >0.5.

According to the principle of the medium, the *Vibrio cholerae* strains, expressing a β-galactosidase activity (use of X-β-galactoside), should produce blue-green colonies, whereas those of *V. parahaemolyticus*, using L-arabinose with acidification of the medium and a colour change of the coloured indicator, should give colonies coloured bright pink. The other genera or species can give violet colonies (use of arabinose associated with a β-galactosidase activity) or colourless colonies (arabinose (−) and β-galactosidase (−)).

4. Reading of the Media:

Coloration Intensity Reading Scale:

It is an arbitrary scale common to all the biological samples and media tested. This scale is valid for this experiment and also for the experiments which will follow. It can be defined in the following way:

| | |
|---|---|
| 0 | corresponds to an absence of activity |
| 0.1 | corresponds to the presence of a trace of coloration |
| 0.5 | corresponds to the presence of a very pale coloration |
| 1 | corresponds to the presence of a clear coloration that is weak in intensity |
| 2 | corresponds to the presence of a definite coloration of medium intensity |
| 3 | corresponds to the presence of an intense coloration |
| 4 | corresponds to the presence of a very intense coloration | a) On Pure Strains

The results are expressed as % correct diagnosis relative to all the tests in terms of sensitivity and specificity after incubation for 24 hours, and are given in the table below, the % sensitivity corresponding to the number of true positives detected on the medium divided by the total number of true positives to be detected, and the % specificity corresponding to the number of true negatives detected on the medium divided by the total number of true negatives to be detected.

| Sensitivity | | Specificity | |
|---|---|---|---|
| V. cholerae | V. parahaemolyticus | V. cholerae | V. parahaemolyticus |
| 100% | 100% | 100% | 95.5 |

These results show, firstly, that all the *Vibrio cholerae* strains indeed give colonies of expected colour (100% sensitivity) and that, secondly, none of the 57 non *V. cholerae* strains develop the characteristic colour of *V. cholerae* (100% specificity). The 4 *V. parahaemolyticus* strains themselves also give colonies having the expected colour (100% sensitivity). Among the 65 non *V. parahaemolyticus* strains, only 3 of them were classified as being false positives (2/2 *Vibrio fluvialis* and 1/2 *Enterobacter aerogenes*) and generate pink colonies characteristic of *V. parahaemolyticus* (95.5% specificity).

b) On Food Matrices

The results presented in the table hereinafter are those observed after incubation at 37° C. for 24 h. Each medium obtained from an artificially contaminated matrix is compared with the control medium (obtained from a food matrix not artificially contaminated) so as to pinpoint, among the associated flora, the bacterial species theoretically used contaminate the food. Each colony thus pinpointed is then isolated and then identified using the conventional test. If the identification is confirmed, the colony is then considered true +, in the opposite case, it is a false +. Moreover, in addition to the colonies of expected colour, an identification is carried out on the other colonies which are not expected but which show a characteristic coloration. If the identification confirms a species belonging to a species other than that expected but which is part of the group *Vibrio cholerae* (*vulnificus*, *mimicus*) or *parahaemolyticus*, it is then a true +, naturally present in the food; on the other hand, if the identification does not confirm *Vibrio cholerae* (*vulnificus*, *mimicus*) or *parahaemolyticus*, the species is considered to be a false +.

| Sensitivity (number of true + obtained over a number of true + expected) | | Specificity (number | |
|---|---|---|---|
| V. cholerae | V. parahaemolyticus | of true + obtained) | Readability |
| 4/4 | 5/5 | 4 to 5 false + | +++ |

All the strains used to contaminate the food matrices were found after pre-enrichment and isolation on the medium according to the invention. The readability of the medium is entirely satisfactory since it is easy to pinpoint the positive, blue-green or pink, colonies in the middle of the associated flora, even if the latter is present in abundance.

5. Advantages of the *Vibrio* ID Medium:

The *Vibrio* ID medium has excellent performance levels in terms of sensitivity and specificity. The readability, i.e. the ability to detect positive colonies or to discard negative colonies, is also very good. The sensitivity is very good in the case of weakly contaminated samples.

The invention claimed is:

1. A culture and identification medium for distinguishing between *cholerae*-group *Vibrio* (*cholerae/vulnificus* and *mimicus*) and *Vibrio parahaemolyticus* bacteria, comprising:
   a substrate for detecting a β-galactosidase enzymatic activity,
   L-arabinose, and
   a neutral red or bromothymol blue colored indicator.

2. The culture and identification medium according to claim 1, wherein the substrate is an X-β-galactoside chromogenic substrate.

3. The culture and identification medium according to claim 2, further comprising a second sugar.

4. The culture and identification medium according to claim 3, wherein the second sugar is glucuronate.

5. The culture and identification medium according to claim 1, wherein the culture and identification medium further comprises a second sugar.

6. The culture and identification medium according to claim 5, wherein the second sugar is glucuronate.

7. A method for isolating and identifying cholerae-group *Vibrio* and *Vibrio parahaemolyticus*, comprising:
   culturing microorganisms on a reaction medium, the reaction medium comprising:
      a substrate for detecting a β-galactosidase enzymatic activity,
      L-arabinose, and
      a neutral red or bromothymol blue colored indicator; and
   reading the reaction medium to detect cholerae-group *Vibrio* and *Vibrio parahaemolyticus*.

8. The method of claim 7, wherein the substrate is an X-β-galactoside chromogenic substrate.

9. The method of claim 7, further comprising a second sugar.

10. The method of claim 9, wherein the second sugar is glucuronate.

* * * * *